(12) United States Patent
Willard-Gallo et al.

(10) Patent No.: US 9,828,644 B2
(45) Date of Patent: Nov. 28, 2017

(54) BACH2 REPRESSION IN CELLS

(75) Inventors: Karen Willard-Gallo, Wavre (BE); Catherine Sibille, Wezembeek-Oppem (BE)

(73) Assignee: UNIVERSITE LIBRE DE BRUXELLES, Bruxelles (BE)

( * ) Notice: Subject to any disclaimer, the term of this patent is extended or adjusted under 35 U.S.C. 154(b) by 115 days.

(21) Appl. No.: 13/878,793

(22) PCT Filed: Oct. 12, 2011

(86) PCT No.: PCT/EP2011/067809
§ 371 (c)(1),
(2), (4) Date: May 8, 2013

(87) PCT Pub. No.: WO2012/049211
PCT Pub. Date: Apr. 19, 2012

(65) Prior Publication Data
US 2013/0338023 A1 Dec. 19, 2013

(30) Foreign Application Priority Data
Oct. 12, 2010 (EP) .................................. 10187271

(51) Int. Cl.
*C12Q 1/68* (2006.01)
*C12N 15/113* (2010.01)

(52) U.S. Cl.
CPC .......... *C12Q 1/6886* (2013.01); *C12N 15/113* (2013.01); *C12Q 1/6841* (2013.01); *C12N 2310/14* (2013.01); *C12Q 2600/118* (2013.01); *C12Q 2600/158* (2013.01)

(58) Field of Classification Search
CPC .. C12Q 1/6841; C12Q 1/6883; C12Q 1/6886; C40B 30/04
USPC ............................................. 435/6.11; 506/9
See application file for complete search history.

(56) References Cited

U.S. PATENT DOCUMENTS 5,627,034 A 5/1997 Gould et al.

FOREIGN PATENT DOCUMENTS

WO WO 2007050495 A2 * 5/2007
WO WO 2009/034481 3/2009

OTHER PUBLICATIONS

Ravoet et al., "6q—is an early and persistent chromosomal aberration in CD3-CD4+ T-cell clones associated with the lymphocytic variant of hypereosinophilic syndrome," Haematologica 2005, 90:753-765.*
Chalandon et al., "Targeting mutated protein tyrosine kinases and their signaling pathways in hematologic malignancies", Haematologica 2005, 90:949-968.*
Baldwin et al., "Upregulation of EphA2 during in vivo and in vitro renal ischemia-reperfusion injury: role of Src kinases," Am. J. Physiol. Renal. Physiol. 2006, 291 :F960-F971.*
Yadav et al., "Fyn Is Induced by Ras/PI3K/Akt Signaling and Is Required for Enhanced Invasion/Migration," Mol. Carcinog. 2011, 50:346-352.*
Ravoet et al., "Molecular profiling of CD3-CD4+ T cells from patients with the lymphocytic variant of hypereosinophilic syndrome reveals targeting of growth control pathways", *Blood*, vol. 114, No. 14, 2009, pp. 2969-2983.
Sakane-Ishikawa et al., "Prognostic Significance of BACH2 Expression Diffuse Large B-Cell Lymphoma: A Study of the Osaka Lymphoma Study Group", *Journal of Clinical Oncology*, vol. 23, No. 31, 2005, pp. 8012-8017.
Brockhoff et al., "Fluorescent mRNA HER2 FISH", *Imaging and Microscopy*, XP009154916, 2010.
Fisher et al., "Comparison of a Standard Regimen (CHOP) With Three Intensive Chemotherapy Regimens for Advanced Non-Hodgkin's Lymphoma", *The New England Journal of Medicine*, vol. 328, No. 14, 2003, pp. 1002-1006.
International Search Report and Written Opinion from International Application No. PCT/EP2011/067809 dated Jan. 5, 2012.
Kamio et al., "B-cell-specific transcription factor BACH2 modifies the cytotoxic effects of anticancer drugs", *Blood*, vol. 102, No. 9, 2003, pp. 3317-3322.
Muto et al., "Activation of Maf/AP-1 Repressor Bach2 by Oxidative Stress Promotes Apoptosis and Its Interaction with Promyelocytic Leukemia Nuclear Bodies", *The Journal of Biological Chemistry*, vol. 277, No. 23, 2002, pp. 20724-20733.
New England BioLabs, "pMal™ Protein Fusion and Purification System", *Version 5.1*, 2003, pp. 1-54.
Ono et al., "Nuclear Positioning of the *BACH2* Gene in BCR-ABL Positive Leukemic Cells", *Genes, Chromosomes & Cancer*, vol. 46, No. 1, 2007, pp. 67-74.
Oyake et al., "Bach Proteins Belong to a Novel Family of BTB-Basic Leucine Zipper Transcription Factors that Interact with MafK and Regulate Transcription through the NF-E2 Site", *Molecular and Cellular Biology*, vol. 16, No. 11, 1996, pp. 6083-6095.
Puthier et al. "Differential expression of Bcl-2 in human plasma cell disorders according to proliferation status and malignancy", *Leukemia*, vol. 13, No. 2, 1999, pp. 289-294.
Sasaki et al., "Cloning and expression of human B cell-specific transcription factor *BACH2* mapped to chromosome 6q15", *Oncogene*, vol. 19, No. 33, 2000, pp. 3739-3749.
Sibille et al., "Genetic and phenotypic characterization of the lymphocytic variant of the hypereosinophilic syndrome: a model of T lymphomagenesis", *Belgian Journal of Hematology*, vol. 1, Issue 2, 2010, pp. 67-70.
Vieira et al., "Transcription Factor BACH2 Is Transcriptionally Regulated by the BCR/ABL Oncogene", *Genes, Chromosomes & Cancer*, vol. 32, No. 4, 2001, pp. 353-363.
Wiznerowicz et al., "Tuning silence: conditional systems for RNA interference", *Nature Methods*, vol. 3, No. 9, 2006, pp. 682-688.
Yarranton, "Inducible vectors for expression in mammalian cells", *Current Opinion in Biotechnology*, vol. 3, No. 5, 1992, pp. 506-511.

* cited by examiner

*Primary Examiner* — Kaijiang Zhang
(74) *Attorney, Agent, or Firm* — Merchant & Gould P.C.

(57) ABSTRACT

A method for measuring the proliferation status of a cell present in a biological sample, comprising the step of measuring in the said cell the loss of BACH2 by Fluorescence after In Situ Hybridization (FISH) analysis and mRNA quantification or by Comparative Genomic Hybridization (CGH) and corresponding kit and applications.

32 Claims, 9 Drawing Sheets

Figure 6
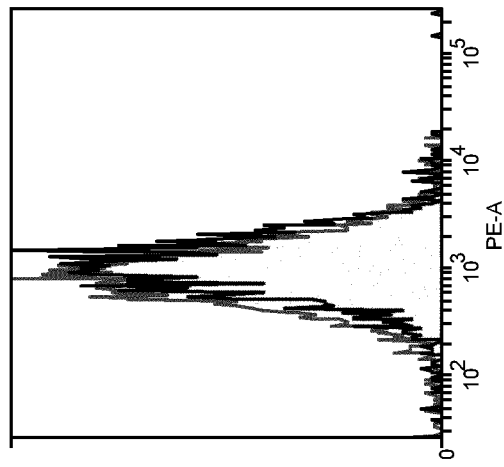
B  FAS expression of untreated clones
   shRNA CTRL A + shRNA BACH2 C
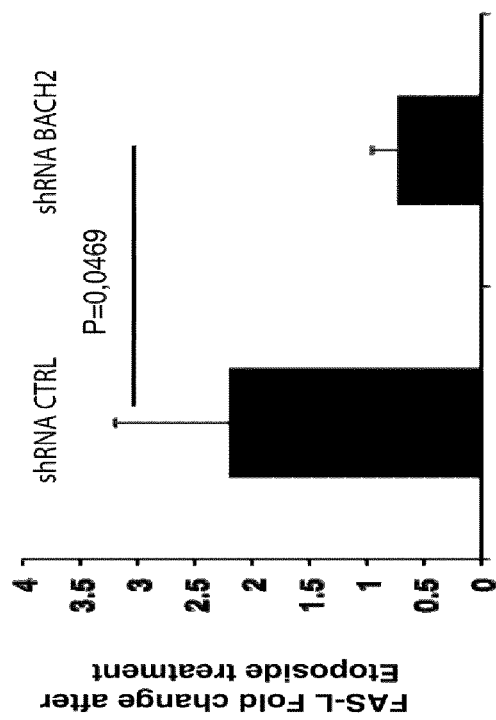
A  Upregulated FAS-L mRNA in shRNA CTRL
   versus shRNA BACH2 clones + Etoposide Figure 6 (continued)
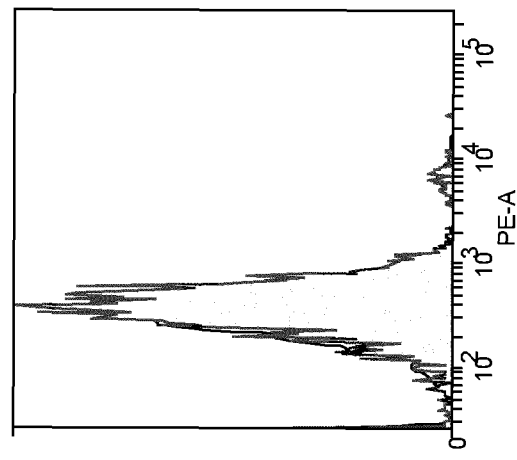
D  FAS-L expression of shRNA BACH2 C
+ Etoposide
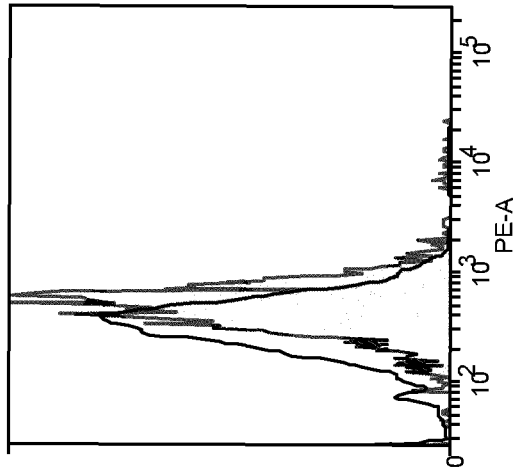
C  FAS-L expression of shRNA CTRL A
+ Etoposide

BACH2 REPRESSION IN CELLS

This application is a National Stage Application of PCT/EP2011/067809, filed 12 Oct. 2011, which claims benefit of Ser. No. 10/187,271.1, filed 12 Oct. 2010 in Europe and which applications are incorporated herein by reference. To the extent appropriate, a claim of priority is made to each of the above disclosed applications.

FIELD OF THE INVENTION

The present invention relates to the field of diagnostic of the proliferation status of a cell.

BACKGROUND OF THE INVENTION AND STATE OF THE ART

Tumour suppressor genes function by restraining cell cycle progression, maintaining genomic integrity or promoting apoptosis.

Chromosomal imbalances are often observed in haematological malignancies and somatic deletions are believed to indicate the location of tumour suppressor genes whose alteration produces loss-of-function in a recessive (Knudson's model) or haploinsufficient (the inactivation of one allele is sufficient to change the phenotype of one cell) context.

The inventors have previously described the occurrence and persistence of hemizigous 6q13-q22 deletions in abnormal CD3-CD4+ T cell clones from two patients suffering from the lymphocytic variant of the hypereosinophilic syndrome (L-HES) over a 6-year study period during which one patient developed a T-cell lymphoma (RAVOET, M. ET AL., 2009. Blood. 114(14), 2969-2983).

Recurrent finding of 6q deletions in various solid tumours and lymphoid diseases has suggested the presence of several tumour suppressor genes residing on the long arm of chromosome 6. The first evidence that 6q loci are involved in tumour suppression came from somatic cell hybrid experiments inducing senescence in fibroblasts and from microcell-mediated chromosome 6 transfer within breast and ovarian cancer cell lines.

Despite heterogeneity, several studies refining the regions of minimal deletion (RMD) in large patient cohorts with lymphoid malignancies highlighted preferential loss of 4 distinct regions at bands 6q14-q15, 6q16-q21, 6q23 and 6q25-27. Notably, deletions of chromosomal bands 6q16-21 are preferentially associated with all of T-lineage and high-grade prostate cancers.

With recent advances in high resolution array-based comparative genomic hybridization (aCGH), a growing number of 6q tumour suppressor genes (such as GRIK2, HACE1, PRDM1, SESN1, REV3L, PTPRK, TNFAIP3/A20, PARK2, . . . ) have been identified at different loci as potential candidates for specific diseases. However, with the exception of the TNFAIP3 (A20) gene, located at band 6q23 and recently recognized as a tumour suppressor gene of B-lineage lymphomas subsets, no definitive evidence of suppressive activity has been obtained for other 6q gene-locus candidates in separate entities.

In human, BTB and CNC homolog 1, basic leucine zipper transcription factor 2 (BACH2) is located at 6q15. This gene is expressed mostly in the thymus, the spleen and leukocytes and at a lower level in the small intestine and the brain. BACH2 mRNA is notably present in pre-B lymphocytes and expressed up to fourfold more strongly in cord blood (UCB) and naïve CD4+CD45RA+ T cells compared to adult CD4+ T cells.

As measured after immunohistochemical analysis, level 2 expression of BACH2 protein represents a worse prognosis for a particular subset of patients suffering from B-cell lymphoma treated with doxorubicin (with no more disclosure about treatment predictivity). The quantification of BACH2 mRNA in the same subsets of patients shows a reduction in the level 2 group, albeit not reaching statistical significance, pointing to the difficulty of analyses based on mRNA quantification of mixture of cancerous cells with non-neoplastic cells (SAKANE-ISHIKAWA ET AL., J. Clin. Oncol. 2005, 23, 8012-8017) and/or to differences between morphological and merely quantitative methods.

SUMMARY OF THE INVENTION

The present invention is related to a method for measuring the proliferation status of a cell (of several cells) present in a biological sample (obtained from a mammal subject, preferably a human patient), this method comprising the step of measuring in the said cell(s) the loss of BACH2 by a (one or two or even three) method selected from the group consisting of Fluorescence after In Situ Hybridization (FISH) analysis, mRNA quantification, immuno-histochemistry (especially when the biological sample is obtained from a (human) solid tumor (and/or from an epithelial cancer) and/or from sarcoma or from a lymph node) and Comparative Genomic Hybridization (CGH), preferably selected from the group consisting of Fluorescence after in situ hybridization (FISH) analysis, mRNA quantification and comparative genomic hybridization (CGH).

Possibly, within the present invention, the loss of BACH2 is the deletion in a cell(s) of one (less preferably of the two) copy of BACH2 gene.

Alternatively, the loss of BACH2 is the deletion of at least 1, 2, 3 exon in one (or, less preferably, in the two) copy of the BACH2 gene, and/or is a mutation in one (or, less preferably, in the two) copy of BACH2 gene, possibly resulting into a defect in RNA splicing.

Preferably, the loss of exon and/or the mutation in BACH2 gene is (positively) correlated with a resulting BACH2 protein having an impaired function.

Preferably, in the method of the present invention, the step of measuring the loss of BACH2 is performed both by FISH analysis (of the said BACH2 gene or of the said BACH2 mRNA) and mRNA quantification (of the said BACH2 mRNA).

The method for measuring the loss of BACH2 may preferably comprise the step of measuring the loss of BACH2 by RNA FISH analysis.

Preferably, in this RNA FISH analysis, 1, 2, or even 3 or 4 probes are used, wherein 1 or 2 probes has (have) a sequence deduced from 1 or 2 BACH2 exon(s) and possibly 1 or 2 (or 3) probes has (have) a sequence deduced from a signalling kinase such as EGFR or HER2 mRNA (or gene) sequence.

Alternatively (or in addition), in the method of the present invention, the step of measuring the loss of BACH2 by CGH is performed (by hybridization) using at least two (3, 4, 5, 6, 7, 8, 9, 10, 11, 12, 13, 14, 15, 20) probes having a length of about 20 to about 80 (preferably of about 60; alternatively of about 22) nucleotides spanning over at least two (3, 4 or even at least 5) exons of the BACH2 gene, possibly, these probes being isolated and labeled.

Alternatively (or in addition), in the method of the present invention, the step of measuring the loss of BACH2 is performed by the measurement of the methylation of BACH2 promotor.

Advantageously, the method of the invention further comprises a first enriching step of the cell(s) (population) to be analyzed from this biological sample.

Advantageously, the method of the invention may further comprise a last deducing step of the proliferation status of the analyzed cell(s) (i.e. a reduced BACH 2 level equates to a worse prognosis).

Advantageously, the method of the invention may further be coupled to the monitoring of a (targeted) therapy (e.g. anticancer), wherein, possibly, a reduced BACH2 level during treatment equates to an ongoing resistance to this treatment (possibly not yet observed upon routine diagnostics and/or histological analysis).

Preferably, in the method of the present invention, the cell(s) to be analyzed is (are) CD4+ T cell(s) and/or CD8+ T cell(s) and/or B cell(s) (more preferably CD4+ T cell(s)).

Preferably the biological sample to be analyzed comprises (consists mainly in) one antigen-specific CD4+ T cell(s) and/or one antigen-specific CD8+ T cell(s) and/or one antigen-specific B cell(s) (being more preferably one antigen-specific CD4+ T cell(s)).

Possibly, in the method of the present invention, the biological sample is obtained from a (human) patient having been submitted to a vaccination or to organ transplantation and, preferably, wherein CD4+ T and/or CD8+ T and/or B cell(s) are (further) enriched by using specific anti-idiotype antibodies, and more preferably wherein the cell(s) is/are CD4+ T cells and/or more preferably wherein the T cell receptor is sequenced.

Alternatively, in the method of the present invention, the biological sample contains stromal cells or (non human embryonic) stem cells, being preferably mesenchymal stem cells.

Alternatively, in the method of the present invention, the biological sample is obtained from a (human) patient suffering of a proliferation disorder, such as cancer, this cancer being possibly a lymphoma or a sarcoma or an epithelial cancer (such as breast, colon and/or prostate cancer). Possibly, the biological sample is obtained from the lymph node and/or from a solid tumor (and/or from an epithelial cancer) and/or from a sarcoma (of a (human) patient suffering from a proliferation disorder).

Alternatively, in the method of the present invention, the biological sample (containing lymphocytes) is obtained from a (human) patient having or suspected to have (or to develop) an auto-immune disease (being preferably selected from the group consisting of rheumatoid arthritis, aplastic anemia, multiple sclerosis, Sjorgen syndrome, allergic diseases (such as asthma or eczema) diabetes, Graves' disease, caeliac diseases (and/or Crohn disease) and lupus erythematosus), a parasitic disease and/or a viral disease. More preferably, this autoimmune disease is rheumatoid arthritis and possibly the biological sample is enriched in CD4+ T cell expressing HLAB27 protein or even more preferably, this autoimmune disease is a caeliac disease (and/or Crohn disease) and possibly the biological sample is enriched in CD8 gamma delta.

Another aspect of the present invention is a diagnostic kit comprising:

means to enrich cells present in a biological sample (being preferably CD4-specific antibodies (and/or CD8-specific antibodies) and means to perform CGH of BACH2 (1, 2, 3, 4, 5, 6, 7, 8, 9, 10, 15 specific nucleotide probes having a length of about 20 to about 80 nucleotides, preferably of about 22 or about 60 nucleotides, spanning over BACH2 sequence, preferably over at least 2, 3, 4, 5 exons of BACH2), these probes being preferably labelled and/or put into a solid support or means to perform FISH analysis of BACH2 and/or means to perform mRNA quantification of BACH2.

Preferably the means to perform FISH analysis comprise an isolated fragment of the (human) BACH2 gene being longer than 2 kbases (preferably, longer than 3, 4, 5 kbases) and spanning over at least one intron and over at least one exon of the said (human) BACH2 gene and, possibly, means to label the said isolated fragment.

Alternatively, other preferred means to perform BACH 2 FISH analysis (and RNA quantification) are means for performing RNA FISH of BACH2, such as 1 or 2 probes that has (have) a sequence deduced from 1 or 2 BACH2 exon(s) and possibly 1 or 2 probes that has (have) a sequence deduced from a signalling kinase such as EGFR and/or HER2 mRNA (or gene) sequence.

Preferably, the means to perform RNA FISH analysis and/or the probes that has a sequence deduced from BACH2 exon or from a signalling kinase comprises a first (hybridizing) nucleotide cassette having sequence of 15 to 100 nucleotides, more preferably of 20 to 50 nucleotides, still more preferably of 20 to 30 nucleotides having at least 95% of identity (or even 100% of identity) with (the complementary strand of) this BACH2 exon or with (the complementary strand of) this signalling kinase.

Advantageously, the means to perform RNA FISH analysis and/or the probes that has a sequence deduced from a BACH2 exon or from a signalling kinase further comprise a second nucleotide cassette (having a sequence not deduced from a BACH2 exon and/or from a signalling kinase) being an (1, 2, 3, 4, 5, 6, 7, 8, 9, 10 or more) oligonucleotide for the signal amplification (in the sense of the bDNA technology) and/or for the visualization of the BACH2 RNA or of the signalling kinase.

Advantageously, when several probes (having different hybridizing cassettes) are used in RNA FISH analysis, different second nucleotides cassettes are coupled to the different first (hybridizing) cassettes (allowing a specific visualization of the probed RNAs or fragments thereof, and being compatible with a multiplex detection).

Another aspect of the present invention is related to a cell (not from human embryo origin) having incorporated a sense and/or an antisense (oligo- or poly-) nucleotide(s) (preferably in the form of a siRNA and/or in the form of a shRNA) corresponding to at least 20 (preferably 21, 22, 23, 24, 25, 26, 27, 28, 29 or at least 30) nucleotide of the mRNA sequence encoding BACH2 (preferably human), these nucleotide sequences being under the control of an inducible promoter, wherein the cell is a recombinant, isolated and/or purified cell.

Preferably, the recombinant and/or isolated and/or purified cell is selected from the group consisting of a (mesenchymal) stem (not human embryonic) cell and/or a stromal cell.

Alternatively, the recombinant and/or isolated and/or purified cell is a B lymphocyte or a T lymphocyte.

Another aspect of the present invention is a topoisomerase (II) inhibitor (etoposide and/or anthracycline) for use in the treatment and/or the prevention of proliferative disorders affecting a (human) patient (such as lymphoma and/or cancer and/or acute lymphoid leukemia especially acute lymphoid leukemia affecting a child), wherein this (human) patient has a normal BACH2 level, or an overexpressed BACH2 mRNA level.

Another aspect of the present invention is related to a medicament selected from the group consisting of immunosuppressant (cyclosporine or anti-CD52), IFNα (not if BACH2 is totally non functional and/or fully deleted) demethylating agents, (not if BACH2 is totally non functional and/or fully deleted), Fas agonist(s), and anti-ras (such as farnesyl transferase inhibitor(s)) for use in the treatment and/or the prevention of proliferative disorders (such as a cancer (sarcoma and/or epithelial) and/or a lymphoma and/or the lymphocytic variant of hypereosinophilic syndrome and/or possibly acute lymphoid leukemia especially acute lymphoid leukemia affecting a child) affecting a (human) patient, wherein this patient has a reduced BACH2 level (preferably in tumoral cell and/or in CD4+ T cells).

Another aspect of the present invention is an immunosuppressant for use in the treatment and/or the prevention of an auto-immune disease (being preferably selected from the group consisting of rheumatoid arthritis, aplastic anemia, multiple sclerosis, Sjorgen syndrome, allergic diseases (such as asthma or eczema) diabetes, Graves' disease, caeliac diseases (and/or Crohn disease) and lupus erythematosus) affecting a (human) patient, wherein this patient has a reduced BACH2 level and, preferably wherein the biological sample obtained from the patient is enriched in CD4+ T cell, more preferably wherein said CD4+ T cells are expressing HLAB27 protein.

Alternatively, a related aspect of the present invention concerns also a medicament selected from the group consisting of immunosuppressant (cyclosporine or anti-CD52), IFNα (not if BACH2 is totally non functional and/or fully deleted) demethylating agents, (not if BACH2 is totally non functional and/or fully deleted), Fas agonist(s), and anti-ras (such as farnesyl transferase inhibitor(s)) for use in the treatment and/or the prevention of proliferative disorders (such as (a solid and/or epithelial) cancer and/or lymphoma and/or the lymphocytic variant of hypereosinophilic syndrome and/or possibly acute lymphoid leukemia especially acute lymphoid leukemia affecting a child) or an auto-immune disease (being preferably selected from the group consisting of rheumatoid arthritis, aplastic anemia, multiple sclerosis, Sjorgen syndrome, allergic diseases (such as asthma or eczema) diabetes, Graves' disease, caeliac diseases (and/or Crohn disease) and lupus erythematosus) affecting a (human) patient, wherein this patient has a reduced BACH2 level (preferably in tumoral cell and/or in CD4+ T cells).

Preferably, in the present invention, a reduced BACH 2 level is the deletion of one copy (not of both copies) of BACH2 gene in a cell, and/or the deletion of at least 1, 2, 3 exon in one (or, less preferably, in the two) copy of the BACH2 gene, and/or a mutation in one (or, less preferably, in the two) copy BACH2 gene, possibly resulting into a defect in RNA splicing.

Possibly, a reduced BACH2 level is (further) measured by a reduction of BACH2 mRNA level in the (enriched) cells present in a biological sample obtained from the patient and/or by immuno-histochemistry of BACH2 protein (especially if the sample is obtained from the lymph node or from a sarcoma or (less preferably) from an solid tumor (and/or from an epithelial cancer) of the patient).

Preferably, the loss of exon and/or the mutation in BACH2 gene is (positively) correlated with a resulting BACH2 protein having an impaired function.

BRIEF DESCRIPTION OF THE FIGURES AND TABLES

Figure 4:
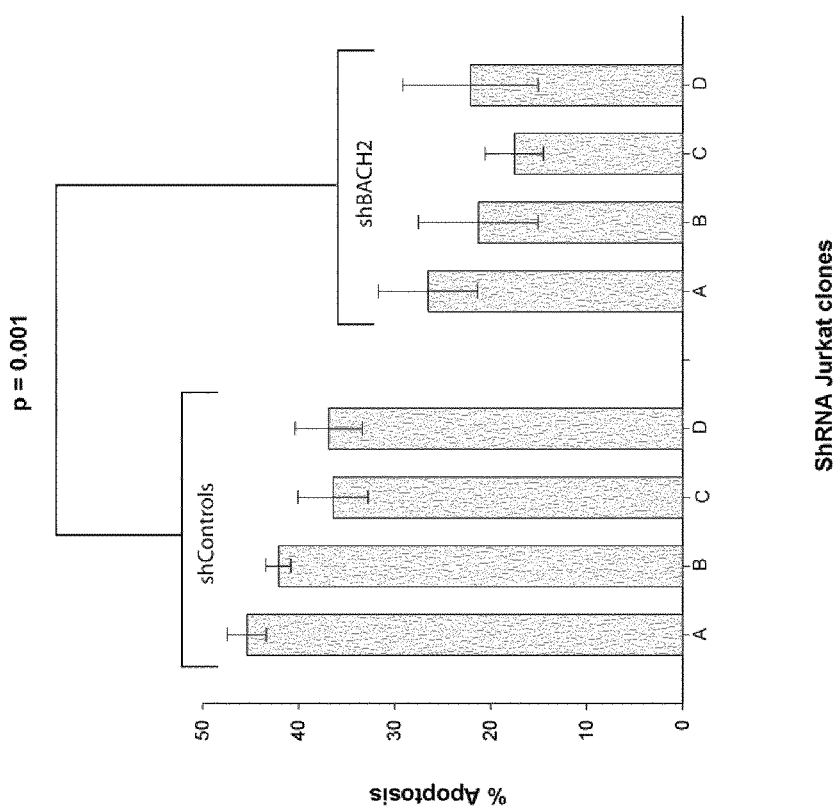

FIG. 4 represents the silencing of BACH2 in Jurkat clones treated with etoposide markedly reduces apoptosis. The 8 clones were incubated for 18 hours with 1.2 µg/ml of etoposide before staining with annexin V-FITC and PI. The apoptosis was assessed by flow cytometry. Columns with standard deviation represent the mean percentage of 3 experiments.

Figure 5:
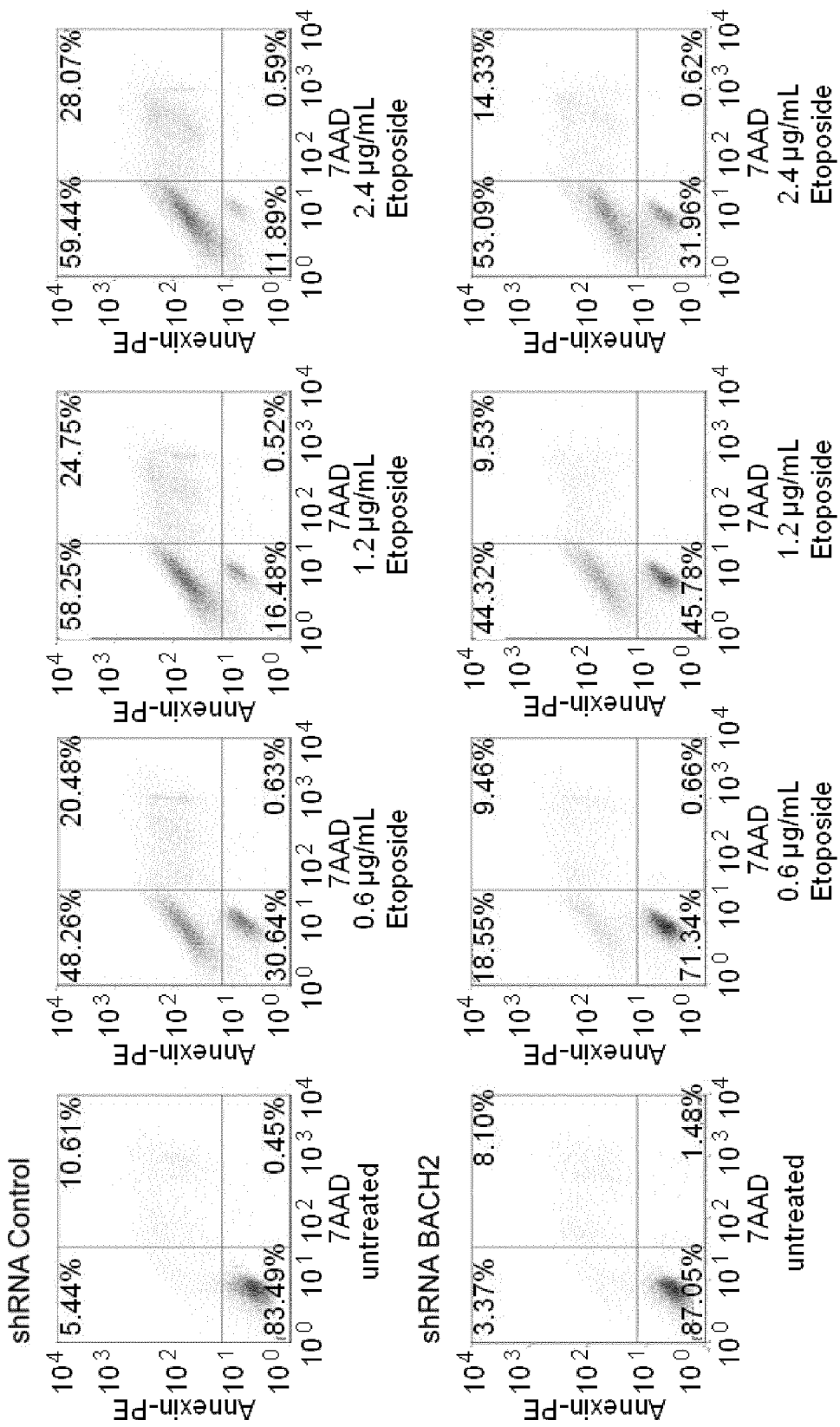

FIG. 5 represents the apoptosis assay of shRNA BACH2 clone C and shRNA CTRL clone A untreated or treated for 18 hours with various concentrations of etoposide before staining with annexin V-FITC and PI. The percentages of apoptotic cells are displayed. The experiment represents a typical example of three individual experiments where p value of the mean of the triplet samples comparison is <0.005 with 1.2 µg/ml concentration of etoposide.

FIG. 6 A represents FAS-L mRNA relative expression of 4 different clones in each group treated for 6 hours with etoposide. In FIGS. 6 B, C and D, Flow cytometric profiles of shRNA BACH2 clone C and shRNA CTRL clone A. Overlay histograms of both clones labelled with anti-FAS antibody (grey histogram) [and with isotype control (open histogram)] are shown in B. Histograms of FAS-L labelled shRNA CTRL clone A and shRNA clone C at 6 hours post etoposide are provided respectively in C and D (grey histogram) with isotype control (open histogram). As shown in D, there is no FAS-L expression induced by etoposide at the surface of shRNA BACH2 clone C in contrast to the upregulated FAS-L expression at the surface of shRNA CTRL A. In B, there is no difference of FAS receptor expression detected between the two clones.

Figure 7:
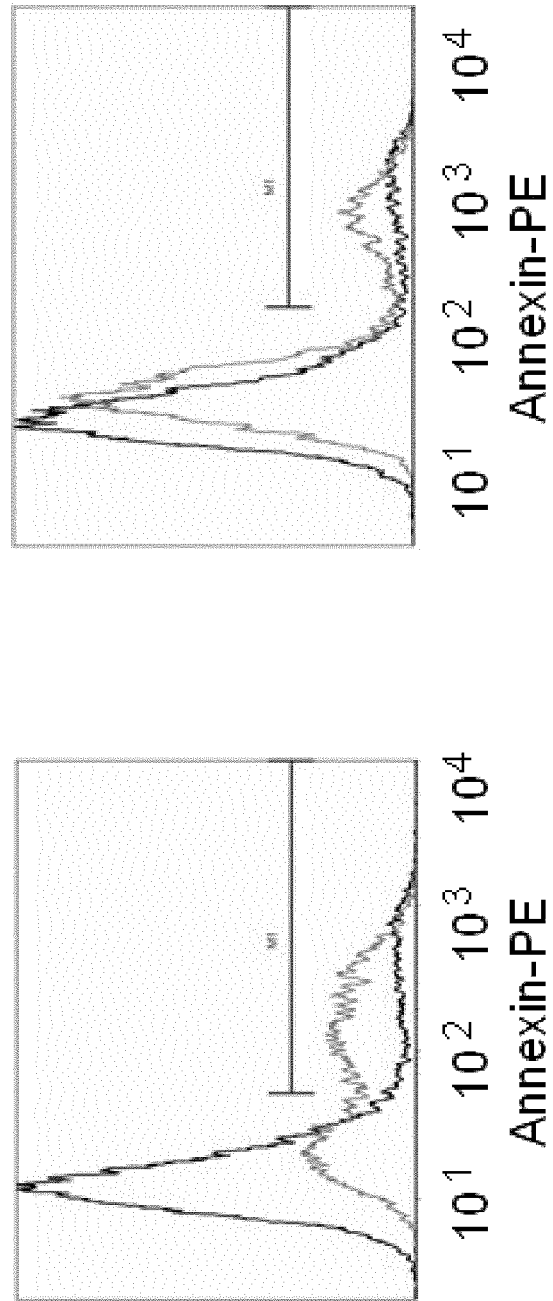
Figure 8:
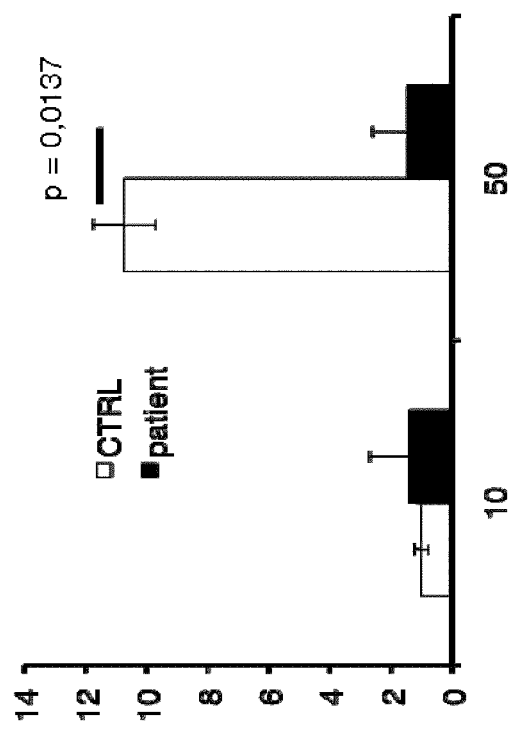

FIG. 7 represents the comparison of apoptosis level of clone shRNA CTRL-A (left panel) or clone shRNA BACH2-C (right panel) untreated (in black) or incubated with 1 µg/ml of etoposide (in grey) during 18 hrs. Histograms of gated cells represent early and late apoptotic populations. As shown in the left panel, 42% of treated shRNA CTRL cells are in apoptosis whereas 18% of apoptotic shRNA BACH2 cells are observed after BACH2 repression FIG. 8 Comparison of Fas L mRNA abundance in control CD4+ cells from a healthy donor and in CD4+ cells from a patient having a hemizigous deletion of BACH2 gene and repression of BACH2 mRNA in function of etoposide treatment. Upon etoposide exposure, the cells having lost one copy of BACH2 fails to produce FasL.

DETAILED DESCRIPTION OF THE INVENTION

The inventors have found that the measurement of the loss of BACH2 gene (and/or a(n) (further) altered BACH2 expression) can be translated into useful diagnostics, then into more apposite treatment(s).

The inventors have further found that the BACH2 measurement should be preferably performed by FISH analysis, advantageously in combination with mRNA quantification. Conversely, measurement restricted to mRNA quantification and to immuno histochemistry have increased risks of having lack of sensitivity and/or of producing false-positive results. They may be used however for analysing biological samples obtained from a (human) solid tumor (and/or from an epithelial cancer) and/or from sarcoma or from a lymph node. Alternatively, CGH analysis of BACH2 (locus) and/or RNA FISH analysis (e.g. as supplied by Panomics/Affymetrix) were found to be both sensitive and accurate.

Immune cells having reduced BACH2 level are more resistant to apoptosis and have increased clonal properties. The inventors found a link between such a reduced BACH2 level and immune-related diseases ranging from (T) lymphomas to auto-immune diseases and cancer such as sarcomas or epithelial cancer (possibly in relation with infiltrated immune cells). Moreover, the measurement of BACH2 level after vaccination (in effectors or memory cells, possibly in relationship with defined idiotypes/clonotypes) helps in predicting the duration of the protection in relation with the persistence of memory cells, while BACH2 measurement in immune cells after organ transplantation is useful in predicting (therefore in preventing upon immunosuppression) adverse events.

It is also useful to measure and/or to modulate BACH2 level in (non human embryonic) stem cells, as this level is in (inverse) relation with their growth properties and/or in (direct) relation with their apoptotic propensities.

Moreover, the inventors found that BACH2 measurement is useful to predict the sensitivity of a (cancer) cell to drugs such as anthracycline or etoposide (preferably etoposide).

The inventors have further combined the measurement at the cell level of BACH2 level and of signalling kinases such as kinases in the ras, Braf, EGFR, Her2, PI3K, AKT, cKIT and merk pathways, preferably EGFR and/or Her2 kinases.

The inventors have also verified that BACH2 level is associated with a prognosis value of a cancer (e.g. epithelial cancer, sarcoma, lymphoma such as T lymphoma) (a decreased BACH2 level representing a worse prognosis) both before treatment and during treatment (such as treatments based on tyrosine kinase inhibitors and/or of growth factor inhibitors and/or of MAP-kinases inhibitors), which allows to switch to another treatment (e.g. chemotherapy) if BACH2 level is decreasing, before the symptoms get worse.

EXAMPLES

Material and Methods
Patients
Five L-HES patients presenting sustained hypereosinophilia with an abnormal circulating CD3-CD4+ T-cell population in their peripheral blood were described previously (Ravoet M. et al., Blood 2009, 114, 2969-83). Informed consent from all patients was obtained in accordance with the declaration of Helsinki and this study was approved by the ethics committees at Hospital St Luc, Hospital Erasme and Institut Jules Bordet.

Cell Line and Culture
E.6.1 Jurkat CD4+ T cell line (Cervantes-Acosta, G., et al. J virological methods 92, 2001, 207-213) kindly provided by O. Ferran, pharmacology unit, Université catholique de Louvain (UCL) was cultivated in RPMI supplemented with 10% Foetal Calf Serum (Gibco).

Cell Purification.
Frozen peripheral blood mononuclear cells (PBMC) from the patients and from 5 healthy donors were purified as previously described (Ravoet et al., 2009) and the isolated population was more than 95% pure CD3-CD4+ and CD3+CD4+, following flow cytometric analysis.

Fluorescence in Situ Hybridization (FISH)
The BAC clone RPI-131H7 located at 6q15 band was provided by the Children's Hospital Oakland (CHORI, BACPAC Resources Center) and selected in the Sequence Maps from the National Center for Biotechnology Information (NCBI). The α-satellite centromeric plasmid D6Z1 specific for the centromere of chromosome 6 was kindly provided by Pr. A. Hagemeijer (Centrum voor Menselijke Erfelijkheid, KUL). Dual-color FISH experiments were performed with FITC-labeled RPI-131H7 BAC probe and with rhodamine-labelled D6Z1 centromeric probe. The threshold of detection for the RPI-131H7 probe calculated by scoring 200 nuclei of purified CD3+CD4+ T lymphocytes from 5 healthy individuals was 6% (mean of the cut-off levels plus three standard deviation). FISH analysis was performed on interphase nuclei of freshly purified CD3-CD4+ T lymphocytes from L-HES P3 and normal CD3+CD4+ T lymphocytes either from P3 or from healthy individuals by using a microscope axioplan 2 imaging (Zeiss). The images were captured with a JAI camera (752×582 pixels) and processed by the Isis3 software (MetaSystems).

RNA Extraction and Quantitative Real-Time PCR (qRT-PCR)
RNA was extracted by the single-step method of isolation with Trizol (Invitrogen). RNA was checked for purity and quantity by using a NanoDrop spectrophotometer (Thermo Fischer Scientific). Total RNA (1 µg) was reverse transcribed with random hexanucleotides using the superscript III First-Strand Synthesis System (Invitrogen) Primers for SENP6 (SUSP1), HMGN3, FAM46A (C6ORF37), RRAGD, BACH2 and SESN1 (Pa26) genes have been described in RAVOET M., ET AL., 2005, Haematologica, 90, 753-765, and primers for EEF1A1, NT5E, SFRS18, SLC16A10, REV3L, FYN, FAM26A, BLIMP1 (PRDM1) and CASC3 (MLN51, endogenous control) were obtained from QIAGEN (QuantiTect Primer Assays, Germany). In addition, primers for ABL gene (endogenous control) were kindly provided by Dr J.-L. VAERMAN (Molecular Biology Unit, Hôpital St Luc, UCL). Quantitative reverse-transcribed polymerase chain reaction (RT-PCR) was performed on a Roche LightCycler® 480 (RocheApplied Science) using SYBR Green PCR Master Mix (Applied Biosystems, Warrington, UK). Analyses were performed using LightCycler® Basic software. For the apoptosis pathway-focused gene expression profiling, the RT$^2$ qPCR-Grade RNA isolation Kit, the RT$^2$ First Strand Kit and the RT$^2$Profiler™ PCR Array System from SABiosciences (Frederick, USA) were used following the manufacturer's protocols.

shRNA BACH2 and shRNA CTRL Transduction into E6.1 Jurkat T Cell Line
The lentiviral constructs shRNA BACH2 (pLenti6.4-CMV-MSGW/EmGFP-miR-NM_021813.1-2405) and shRNA CTRL (pLenti6.4-CMV-MSGW/EmGFP-miR-neg) were purchased by the Invitrogen custom services. The shRNA BACH2 (pLenti6.4-CMV-MSGW/EmGFP-miR- NM_021813.1-2405) was produced by cloning the 2405 to 2425 miR nucleotide sequences from the NM_021813.1 BACH2 gene genomic sequence (NCBI) into the Gateway® Destination vector pLenti6.4/R4R2/V5-DEST following prior selection by using the BLOCK-iT RNAi Target screening System giving 90% knockdown activity relative to the miR-negative control (Invitrogen).

Gene Transduction into E6.1 Jurkat Cells

Exponentially growing cells were seeded overnight at a density of $0.5 \times 10^6$ cells per well in 24 well plates with complete RPMI 1640 medium. Cells were then placed into precoated culture dish with recombinant human fibronectin fragment RetroNectin and then transduced with $2.0 \times 10^6$ particles/ml (MOI=4) of each lentiviral construct according to the manufactures instructions (Takara Bio, Inc.). Stable transfectants were selected in medium containing 10 microgram per mL of blasticidin (Invitrogen) and single cell clones were established by using FACS sorting of the eGFP positive population.

Plasmids

BACH2-pCDNA3 encoding the human BACH2 cDNA was kindly provided by Professor Etsuro Ito, Department of Pediatrics, Hirosaki University, Japan. BACH2-pCDNA3 or pCDNA3 transfection assays were performed according to the manufacturer's conditions required for E6.1 Jurkat cell electroporation (Amaxa Biosystems) and transfectants were selected in complete RPMI 1640 medium containing 1 mg per mL of G418 (GIBCO). Single cell clones were obtained by the limiting dilution method.

Example 1

Gene Expression Profile Focused on the 6q13-22.1 Minimal Deleted Region in CD3-CD4+ T Cells from 3 L-HES Patients A commonly deleted region located between bands q13 and q22.1 of the long arm of chromosome 6 was previously identified in CD3-CD4+ T cells from 2 L-HES patients (P1 and P2). To complete the genomic characterization of the CD3-CD4+ T cell clone of a third patient (P3), FISH experiments were performed using a 6q15-specific BAC probe. A complete 6q loss was identified in 25% of nuclei of uncultured CD3-CD4+ T cells from patient P3 and found associated with an isochromosome 6p (i(6) (p10;p10)) as confirmed by CGH.

By comparing the gene expression profiles of CD3-CD4+ T cell clones from 3 L-HES patients with CD3+CD4+ T cells from healthy controls, the inventors have detected 13 repressed genes within the commonly deleted region 6q13-q22.1.

No enhanced expression was found even in the totality of the long arm of chromosome 6, in contrast to several over-expressed transcripts of the 6p short arm such as HLADR and RUNX2 genes. Thus, with stringent statistical analysis, the only modified pattern of gene expression relative to controls observed from cytoband 6q13 to 6q22.1 is a common repression or loss of namely: EEF1A1, SENP6, HMGN3, FAM46A, NT5E, RRAGD, BACH2, SFRS18, SESN1, SLC16A10, REV3L, FYN and FAM26A genes.

Example 2

Gene Expression Analysis of the 6q13-22.1 Region Extended to a Cohort of 5 Patients L-HES The validation of the microarray data was performed for the 13 mentioned genes by real-time quantitative RT-PCR on purified T cells from an enlarged patient cohort of 5 L-HES patients and 5 healthy controls (Table 1).

TABLE 1

| Gene Symbol | Cytoband | Average DCt 5 Patients | Rank 5 Patients | Average DCt 5 Controls | Rank 5 Controls | Average $2^{(-DDCt)}$ 5P vs 5C | Fold Change 5P vs 5C | p-value 5P vs 5C |
|---|---|---|---|---|---|---|---|---|
| NM_001402.5 | EEF1A1 | 6q13-14 | −6.64 | [−9.73:−5.55] | −9.06 | [−9.31:8.87] | 0.19 | −5.38 | 0.0155 |
| NM_00100409.1 | SENP6 | 6q14.1 | 1.73 | [0.91:2.59] | −0.09 | [−0.48:0.38] | 0.28 | −3.54 | 0.0007 |
| NM_004242.2 | HMGN3 | 6q14.1 | 1.92 | [−0.54:4.08] | −0.50 | [−0.72:−0.3] | 0.19 | −5.34 | 0.0143 |
| NM_017633.2 | FAM46A | 6q14.1 | 5.63 | [1.88:7.95] | 2.67 | [2.33:2.86] | 0.13 | −7.73 | 0.0192 |
| NM_002526.2 | NT5E | 6q14.3 | 9.38 | [6.65:11.19] | 4.94 | [3.12:6.25] | 0.05 | −21.74 | 0.0012 |
| NM_021244.4 | RRAGD | 6q15 | 5.98 | [3.14:7.19] | 2.53 | [1.98:2.78] | 0.09 | −10.97 | 0.0021 |
| NM_021813.2 | BACH2 | 6q15 | 4.73 | [2.41:6.83] | 1.22 | [0.64:1.66] | 0.09 | −11.42 | 0.0019 |
| NM_01591.1 | SFRS18 | 6q16.3 | −0.47 | [−0.98:0.63] | −2.93 | [−3.2:2.34] | 0.18 | −5.50 | 0.0001 |
| NM_014454.1 | SESN1 | 6q21 | 3.86 | [1.88:4.83] | 0.98 | [0.41:1.4] | 0.14 | −7.36 | 0.0008 |
| NM_018593.4 | SLC16A10 | 6q21 | 7.66 | [4.64:9.85] | 2.38 | [1.97:2.71] | 0.03 | −38.96 | 0.0025 |
| NM_002912.3 | REV3L | 6q21 | 3.51 | [2.49:4.5] | 1.07 | [0.38:1.72] | 0.18 | −5.43 | 0.0003 |
| NM_002037.3 | FYN | 6q21 | −1.18 | [−2.39:−0.06] | −2.52 | [−2.69:2.35] | 0.39 | −2.54 | 0.0114 |
| NM_001010919.1 | FAM26F | 6q22.1 | 5.41 | [0.79:8.65] | 3.35 | [2.34:4.09] | 0.24 | −4.16 | 0.3140 |

Table 1. Statistically significant reduction in 12 genes expression validated by real-time quantitative RT-PCR among 5 patients L-HES. Results are normalized with average of the 5 healthy control.

Except for FAM26F (p=0.314) a significant p-value was obtained for the 12 remaining genes, confirming repression or loss of their corresponding mRNA (Table1).

The minimal deleted region previously defined in two L-HES patients extending from band 6q13 to q22.1 covers 301 common genes and ESTs (Entrez Map viewer human Genome browser built 37.1). If EEF1A1 and FAM26F genes are excluded because of reported oncogenic properties for the first and lack of statistical significance for the second (p<0.314), 11 genes of interest are significantly down regulated between 6q14.1 and 6q21 bands in a 35,88 Mb region. The newly defined region extends from the SENP6 gene located proximally at 74,225,473 bp to the FYN gene distally positioned at 112,194,627 bp.

Example 3

Gene Expression of the 6q14.1-22.1 Region During P1 Clinical Evolution

The chronological profiling of CD3-CD4+ T-cells from P1 was previously described starting at the chronic indolent clinical phase and continuing to the full blown T lymphoma stage.

The inventors measured over time the progressive changes in expression of the genes contained within the 6q14.1-22.1 region during the disease to understand the transforming steps.

Figure 1:
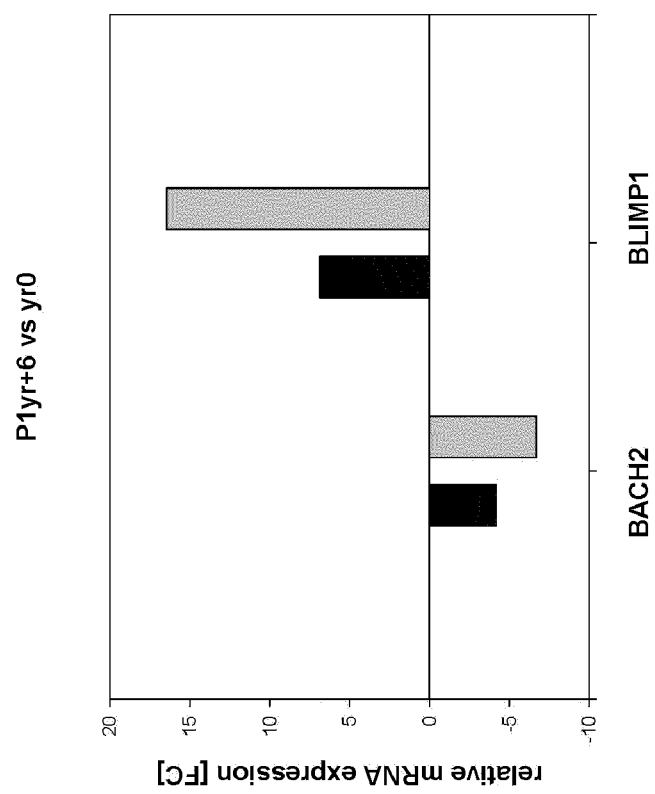
FIG. 1 represents a real-time quantitative RT-PCR showing progressive over-repression of mRNA BACH2 and over-expression of mRNA BLIMP1 during clinical evolution of P1. After normalization with the average of 8 controls, fold change of BACH2 and BLIMP1 genes expression are indicated at yr 0, in black, and at yr+6, in grey, respectively.

Of the 11 repressed genes, only BACH2's transcript level was shown significantly and progressively over-repressed when tested by microarray and by real-time quantitative RT-PCR (FIG. 1). In particular, a ~1.7 fold additional decrease in BACH2 mRNA level was confirmed between yr 0 and yr+6 corresponding, respectively, to samples taken during the chronic and acute phases of the disease (FIG. 1).

Of interest, at that advanced stage, BACH2 over-repression was associated with a significant 2.4 fold over-expression of BLIMP1 mRNA (microarray, p=0.0001) located precisely at band 6q21 of the same deleted region (FIG. 1). However, contrasting with BACH2 (p=0.0019), the level of BLIMP1 mRNA was not increased during the chronic phase of the 5L-HES patients relative to the 5 healthy controls (p=0, 18) suggesting that it represents a secondary or late event associated with the progression of P1 disease. Therefore, while BACH2 repression occurs at early stages of the disease, these two genes appeared to be epigenetically and inversely regulated since they are both located on the same hemizigous deleted region.

Example 4

Comparison of the Expression Level of BACH2 mRNA in Normal and L-HES T Lymphocytes The repression of BACH2 gene in CD3-CD4+ TH2 cells of L-HES patients was detected by reference to polyclonal CD3+CD4+ T cells purified from healthy controls.

Because of the heterogeneity of these CD3+CD4+ T cell populations a clonal artefact may explain these findings.

The inventors next verify whether similar repression could be observed when comparing the abnormal CD3-CD4+ T cells with antigen-specific CD3+CD4+ T helper clones or various CD4+ sub-sets. The relative expression of BACH2 was found significantly decreased in the group of 3 CD3-CD4+ T cell clones from L-HES patients versus the group of 3 CD3+CD4+ T helper antitumor clones (p=0.0023). Moreover, expression of BACH2 mRNA in, respectively, one CD4+ Treg clone, one CD8+ T effector clone and purified memory CD4+ CD45RO+ T cells from a healthy control was found to be 5 to 10 fold higher relative to the 3 CD3-CD4+ T cell clones.

Example 5

Molecular Analysis of the BACH2 Gene in CD3-CD4+ T Cell DNA from 2 L-HES Patients To identify possible mutations at the BACH2 locus within the remaining allele, sequence analysis was performed on DNA extracts from CD3-CD4+ T cells of P1 and P3 displaying heterozygous deletion in the 6q15 region. However, for both patients, only wild-type sequences of the coding exons of BACH2 gene were obtained.

Example 6

Molecular Analysis of the BACH2 gene in CD3-CD4+ T Cell DNA

The inventors then searched for possible mutations in the BACH2 locus within the remaining allele. The sequence analysis was performed on DNA extracts from CD3-CD4+ T cells of P1 and P3 displaying heterologous deletion in the 6q15 region.

For both patient, only wild-type sequences of the coding exons of BACH2 gene were obtained.

The inventors further searched for the methylation of the BACH2 promoter sequences. Following amplification, bisulfite treatment and subcloning of CD3-CD4+ DNA from patient P3, no specific promoter region was found to be hypermethylated compared with CD3+CD4+ T cells from healthy (control) patients.

Example 7

Transduction of BACH2 shRNA BACH2 into the Jurkat E6.1 Cell Line

Primitive CD3-CD4+ T cells from L-HES patients are available in restricted amounts and rapidly undergo apoptosis in vitro. This extreme fragility of CD3-CD4+ T cells from L-HES patients hampered the efficient re-introduction of BACH2 gene by means of transfection experiments using vectors encoding the complete BACH2 cDNA sequence (BACH2-pCDNA3).

CD3+CD4+ E6.1 Jurkat T cell line was next used for functional assays. However, transfections with BACH2-pCDNA3 aiming at reinforced expression of BACH2 in Jurkat cells, resulted in the suppression of E6.1 clonogenicity as observed by the total absence of BACH2-pCDNA3 growing transfectants in contrast to control clones (with pCDNA3 vector alone).

Next, the inventors turned to the use of small hairpin RNAs (shRNAs) for the targeted repression of gene expression.

Since BACH2 protein expression in E6.1 cell was found to be identical to normal helper T cell clones, and since no 6q deletion was identified in this cultured cell line, it appeared as an ideal recipient cell for assessing the potential tumour suppressive properties of BACH2 by shRNA silencing.

For this purpose, a BACH2 shRNA lentiviral vector was designed by inserting miR RNAi sequence spanning position 2405 bp to 2425 bp of BACH2 gene in pLenti6.4/R4R2/V5-DEST (Invitrogen). Two successive cycles of lentiviral infection of E6.1 with, respectively, BACH2 shRNA or a negative control shRNA preceded cloning of EGFP-positive cells by FACS sorting.

Figure 2:
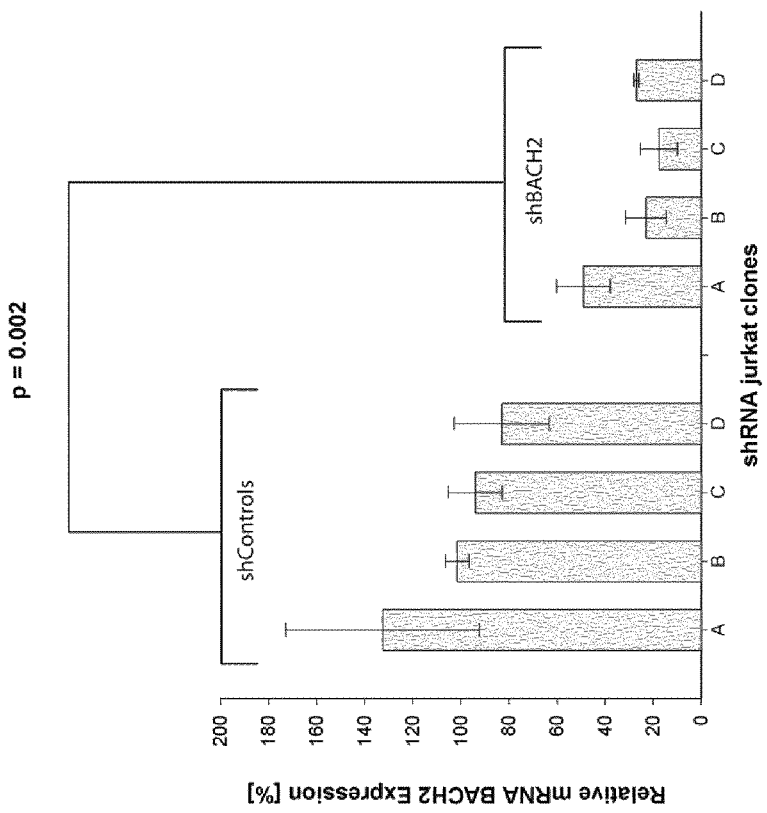
FIG. 2 represents the relative mRNA BACH2 expression level in Jurkat T cell line transduced with control shRNA or BACH2 shRNA lentiviral vectors (4 clones shCTRL-A,B,C,D and 4 clones shBACH2-A,B,C,D respectively). Columns with standard deviations represent the mean percentage of 3 experiments.

As illustrated in FIG. 2, a representative panel of 4 transduced E6.1 clones was generated, with silencing at different levels of BACH2 transcript compared to the negative controls (p=0.002). Clonogenicity was always superior in the shRNA BACH2 group as the number of shRNA BACH2 clones was at least twice the shRNA control clones (>50%).

However, BACH2 repression does not affect the growth properties of the cloned cells.

Figure 3:
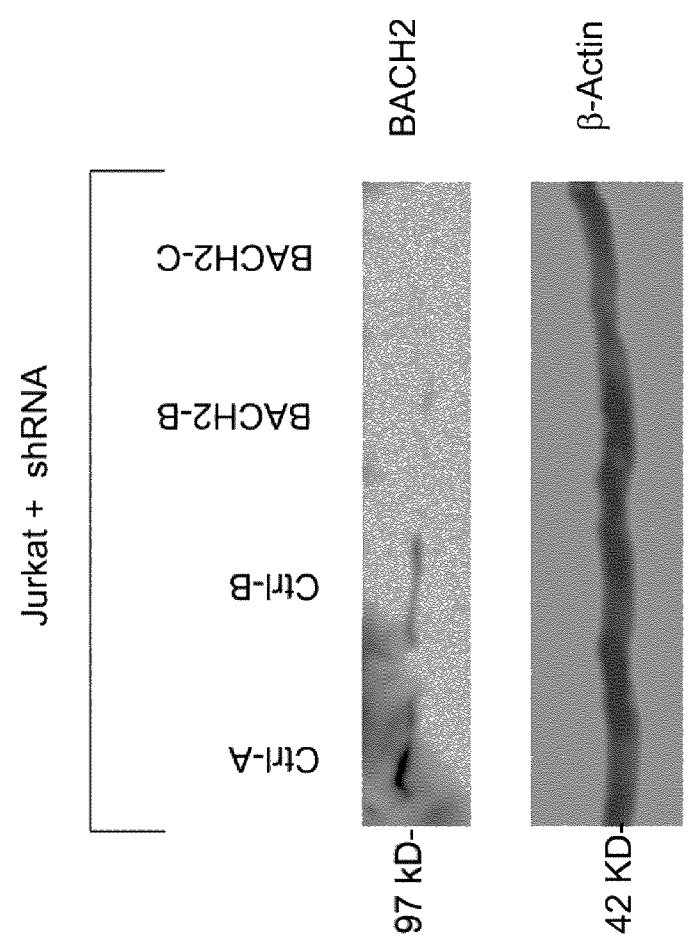
FIG. 3 represents the extinction of BACH2 protein in shRNA BACH2 C,D Jurkat clones versus shRNA BACH2 A,B clones measured by western blotting. BACH2 protein is detected in the 2 shRNA control lanes and absent in the shRNA BACH2-B and -C lanes in contrast to Beta-actin endogenous expression.

Western blotting with cell extracts from shRNA CTRL-A, -B clones compared to shRNA BACH2-B, -C were performed with specific anti-BACH2 monoclonal antibodies and confirmed the extinction of BACH2 protein in the 2 shRNA silenced clones (FIG. 3).

Example 8

Apoptotic Resistance of BACH2 shRNA Jurkat Clones to Topoisomerase Inhibitor VP16

The inventors firstly added FAS ligand (FASLG/TNFSF6) or PMA (phorbol myristic acetate) (see Table 2) to control or to cells transfected with BACH2 sh RNA. They further treated control and transfected cells (with BACH2 sh RNA) by a 18-hours stimulation with anti-CD2, anti-CD28 or anti-CD3 antibodies.

TABLE 2

| | Apoptosis response % | | | |
|---|---|---|---|---|
| Treatment | shRNACTRL | shRNABACH2 | Difference % | p |
| PMA | 16.17 (+/−2.26) | 16.7 (+/−6.12) | −0.5 | 0.928 |
| Fas-L | 33.18 (+/−2.32) | 34.51 (+/−3.75) | −1.3 | 0.719 |
| Etoposide | 41.2 (+/−4.94) | 18.27 (+/−2.71) | 23 | 0.013 |

Table 2. Apoptosis analysis of shRNA BACH2 and shRNA CTRL Jurkat clones treated with etoposide, PMA and Fas-L ligand. In contrast to etoposide treatment, no significant difference of apoptosis is observed with adjunct of Fas-L or PMA.

The inventors did not notice any difference in apoptosis in the two conditions triggered by Fas ligand and conclude after this round of experiments that BACH2 repression would be of no help in protecting cells from apoptosis.

Etoposide (VP16), commonly used for treatment of non-Hodgkin lymphomas (NHL), induces intracellular oxidative stress by inhibiting topoisomerase II thereby generating DNA-strand breaks followed by cell apoptosis.

The addition of Etoposide to control Jurkat cells resulted into apoptosis of these cells, as it was the case for Fas ligand addition.

The inventors however further tested if BACH2 silencing could modify resistance to apoptosis of Jurkat T cell clones treated with etoposide.

Data presented in FIG. 4 indicate that, surprisingly, the 4 BACH2 shRNA clones are on average twice as resistant to apoptosis as the 4 control clones (p=0.001) following etoposide treatment.

Moreover, a correlation could be drawn between the level of mRNA BACH2 repression and the level of apoptosis resistance observed for each clone ($R^2$=0.9251). Comparison between clone shRNA BACH2-C and shRNA control-A presenting the same mean fluorescence intensity of EGFP demonstrated a two-fold reduction in the number of apoptotic cells (AnnexinV+) in the BACH2-repressed clone at 1 µg/ml of etoposide.

Further, serial etoposide dilutions demonstrated 30% to 70% gain in apoptosis resistance of clone shRNA BACH2-C relative to clone shRNA CTRL-A (FIG. 5).

Example 9

Comparative Apoptosis Gene-Array Profiling of Jurkat shRNA BACH2 Clone C Versus shRNA CTRL Clone A Obtained at 6 h Post-Etoposide Treatment In order to define specific genes implicated in the apoptotic resistance of BACH2-silenced Jurkat cells relative to controls, comparative gene expression profiling was performed by using the apoptosis focused $RT^2$ profiler PCR array system (Sabiosciences).

The genes in shRNA BACH2-C cells showing significantly modified expression compared with shRNA CTRL-A cells are indicated in Table 3 with specific functions related to apoptosis.

Jurkat shRNA CTRL clone A following 4 hours incubation with 1.2 µg/ml etoposide or without treatment.

Notably, at 6 hours post-etoposide induction, silencing of BACH2 is essentially associated to repression of 4 pro-apoptotic genes such as BIK, CASP1, FAS-L, RIPK2 and of one mediator, CARD6, without upregulation of survival genes.

Example 10

Comparative Cytometric FAS/FAS-L Profiles of Jurkat shRNA BACH2 Clone C Versus shRNA CTRL Clone A Obtained at 6 h Post-Etoposide Treatment The inventors further verify both constitutive and induced level of expression of the relevant FAS/FAS-L protein in these cells compared to controls.

As shown in FIG. 6A, significant repression (p=0.0469) of the FAS-L was observed in silenced BACH2 clones under genotoxic stress. As generally observed in the absence of activation via the antigen receptor or exogenous cytotoxic stimulus, no constitutive FAS-L was observed at the surface of untreated CD4+ Jurkat T cell clones. However, at 6 hours post-etoposide treatment, the flow cytometric analysis with antibody to FAS-L detected upregulated FAS-L on shRNA control cells (FIG. 6C) but no upregulation on shRNA BACH2 clone C (FIG. 6D). These FACS data revealing the absence of FAS-L were thus consistent with the transcriptional inhibition of the FASL gene in the BACH2-silenced Jurkat cells identified by quantitative RT-PCR at 6 hours post-etoposide (Table 3; FIG. 6A). Moreover, the constitutive Fas expression shown here and previous apoptosis experiments carried out with FAS-L adjunct (Table 2), did not show alteration of Fas receptor signalling in the BACH2-silenced Jurkat clones, indicating that only the FAS-L pathway was deregulated in the absence of BACH2 upon genotoxic activation.

This observation is further confirmed by the ex-vivo analysis shown at FIG. 8, wherein, clearly, CD4+ T cells having hemizigous BACH2 fail to express FasL mRNA.

This lack of expression of FasL results into deficience in etoposide-induced apoptosis (FIG. 7)

The invention claimed is:
1. A method comprising the steps of:
measuring in a cell present in a biological sample from a patient, the loss of BACH2 by both Fluorescence after in situ hybridization (FISH) analysis and mRNA quantification, or by comparative genomic hybridization (CGH) and,
wherein the measuring is associated with a proliferation disorder, an auto immune disease, a vaccination or an

TABLE 3

| Gene number | Name | Function | Fold change |
|---|---|---|---|
| NC_000022.10 | BIK | BCL2-interacting killer, intrinsic apoptosis-inducing, shares a BH3 domain as BAX and BAK proteins | −3.3 |
| NC_000005.9 | CARD5 | caspase recruitment domain family, member 6, positively modulates signalling converging on activation of NF-kB | −2.6 |
| NC_000011.9 | CASP1 | apoptosis-related cysteine peptidase (interleukin 1, beta, convertase) plays a central role in the execution-phase of cell apoptosis | −2.1 |
| NC_000001.10 | FAS-L | Fas ligand (TNF superfamily, member 6), extrinsic apoptosis-inducing binds Fas receptor | −4.6 |
| NC_000008.10 | RIPK2 | receptor-interacting protein (RIP) family of serine/threonine protein kinases, potent activator of NF-kappaB and inducer of apoptosis | −2 |

Table 3. Comparison of relative mRNA expression of apoptosis related genes in Jurkat shRNA BACH2 clone C versus organ transplantation, when the BACH2 loss is characterized by a cell BACH2 expression level which is at least 1.7 fold decrease compared to an expression level of a cell of an healthy individual.

2. The method of claim 1, wherein the step of measuring the loss of BACH2 is performed both by FISH analysis and mRNA quantification.

3. The method of claim 1, wherein the step of measuring the loss of BACH2 is performed by RNA FISH analysis and wherein 1 or 2 probes has (have) a sequence deduced from 1 or 2 BACH2 exon.

4. The method of claim 1, wherein the step of measuring the loss of BACH2 by CGH is performed by hybridization with at least two probes having a length of 20-80 nucleotides spanning over at least two exons of the BACH2 gene.

5. The method according to claim 1, further comprising a first enriching step of the cell population obtained from the biological sample.

6. The method according to claim 1, wherein the cell is a CD4+ T cell.

7. The method of claim 6, wherein the biological sample comprises one antigen-specific CD4+ T cell or CD8+ T cell.

8. The method according to claim 1, wherein the biological sample is obtained from a human patient suffering of a proliferation disorder.

9. The method according to claim 1, wherein the biological sample is obtained from a human patient having been submitted to a vaccination or to organ transplantation.

10. The method according to claim 1, wherein the biological sample is obtained from a human patient having or suspected to have or to develop an auto-immune disease.

11. The method according to claim 1, wherein the biological sample contains non human embryonic stem cells or stromal cells.

12. The method according to claim 1, wherein the cell is CD8+ T cell.

13. The method according to claim 1, wherein the cell is a B cell.

14. The method according to claim 1, wherein the measuring is associated with cancer selected from the group consisting of epithelial cancer, sarcoma or lymphoma.

15. The method of claim 1, further comprising the steps of: performing RNA and/or FISH analysis of a signalling kinase; and administering to the patient compounds selecting from the group consisting of a tyrosine kinase inhibitor, a growth factor inhibitor and/or a MAP kinase inhibitor.

16. The method of claim 15, wherein the signalling kinase is a growth factor.

17. The method of claim 16, wherein the growth factor receptor is EGFR and/or HER2.

18. The method according to claim 15, wherein the signaling kinase is associated with pathways selected from a group consisting of ras, Braf, EGFR, Her2, PI3K, AKT, cKIT and merk.

19. The method according to claim 15, wherein the signaling kinase is encoded by the FYN gene.

20. The method according to claim 1, wherein the measuring is associated with a prognosis value of cancer before or after treatment of said cancer.

21. The method according to claim 1, wherein the patient suffers from a proliferation disorder; and wherein the measuring is associated with a prognosis value of cancer before or after treatment of said cancer.

22. The method according to claim 1, wherein the FISH analysis is performed using a BAC probe and/or a D6Z1 probe.

23. The method according to claim 22, wherein the BAC probe is a 6q15-specific BAC probe.

24. The method according to claim 1, further comprising the step:
Delivering a medicament to a human patient from which the biological samples was obtained, the medicament selected from the group consisting of immunosuppressant, IFNα, Fas agonist(s) and farnesyl transferase inhibitor(s), thereby treating or preventing a proliferative disorder or auto-immune disorder of the human patient, wherein the measuring of BACH2 levels indicates a reduced BACH2 level.

25. The method of claim 1, further comprising the step of performing RNA and/or fish analysis of signaling kinases.

26. The method of claim 1, wherein the loss of BACH2 is the deletion in a cell of one copy of the BACH2 gene.

27. The method of claim 1, wherein the loss of BACH2 is the deletion in a cell of the two copies of the BACH2 gene.

28. The method of claim 1, wherein the loss of the BACH2 is the deletion of at least 1, 2 or 3 exon(s) in one copy of the BACH2 gene.

29. The method of claim 1, wherein the loss of the BACH2 is the deletion of at least 1, 2 or 3 exon(s) in the two copies of the BACH2 gene.

30. The method of claim 1, wherein the loss of BACH2 is a mutation in one copy of the BACH2 gene.

31. The method of claim 1, wherein the loss of the BACH2 is a mutation in the two copies of the BACH2 gene.

32. The method of claim 1, wherein the step of measuring the loss of BACH2 is performed by the measurement of BACH2 promoter methylation.

* * * * *